(12) United States Patent
Sano et al.

(10) Patent No.: US 12,414,908 B2
(45) Date of Patent: Sep. 16, 2025

(54) COSMETIC

(71) Applicants: Sano Co., Ltd., Osaka (JP); Daio Paper Corporation, Ehime (JP)

(72) Inventors: Norio Sano, Osaka (JP); Hiroto Sasaki, Ehime (JP); Aya Fujita, Tokyo (JP); Daiki Yoshihara, Tokyo (JP)

(73) Assignees: Sano Co., Ltd., Osaka (JP); Daio Paper Corporation, Ehime (JP)

( * ) Notice: Subject to any disclaimer, the term of this patent is extended or adjusted under 35 U.S.C. 154(b) by 565 days.

(21) Appl. No.: 17/289,437

(22) PCT Filed: Dec. 25, 2019

(86) PCT No.: PCT/JP2019/050767
§ 371 (c)(1),
(2) Date: Apr. 28, 2021

(87) PCT Pub. No.: WO2020/138144
PCT Pub. Date: Jul. 2, 2020

(65) Prior Publication Data
US 2021/0393502 A1 Dec. 23, 2021

(30) Foreign Application Priority Data
Dec. 27, 2018 (JP) .................................. 2018-245915

(51) Int. Cl.
| | |
|---|---|
| *A61K 8/73* | (2006.01) |
| *A61K 8/02* | (2006.01) |
| *A61P 1/00* | (2006.01) |
| *A61Q 1/00* | (2006.01) |

(52) U.S. Cl.
CPC .............. *A61K 8/731* (2013.01); *A61K 8/027* (2013.01); *A61Q 1/00* (2013.01)

(58) Field of Classification Search
CPC ........... A61K 8/731; A61K 8/027; A61Q 1/00
See application file for complete search history.

(56) References Cited

U.S. PATENT DOCUMENTS

| | | | | |
|---|---|---|---|---|
| 6,534,071 | B1 * | 3/2003 | Tournilhac | A61K 8/02 |
| | | | | 424/70.6 |
| 6,541,627 | B1 * | 4/2003 | Ono | D21H 19/42 |
| | | | | 536/124 |
| 9,283,160 | B2 * | 3/2016 | Herzog | A61K 8/494 |
| 2002/0192251 | A1 * | 12/2002 | Collin | A61K 8/027 |
| | | | | 424/443 |
| 2011/0305650 | A1 | 12/2011 | Herzog | |
| 2012/0308624 | A1 * | 12/2012 | Isogai | A61K 8/345 |
| | | | | 424/401 |
| 2017/0065514 | A1 * | 3/2017 | Crofoot | A61Q 5/02 |
| 2018/0078484 | A1 | 3/2018 | Blell et al. | |
| 2018/0296446 | A1 | 10/2018 | Homma et al. | |
| 2019/0060205 | A1 | 2/2019 | Jun et al. | |
| 2020/0115471 | A1 * | 4/2020 | Tsujii | C08L 101/00 |

FOREIGN PATENT DOCUMENTS

| | | |
|---|---|---|
| JP | 11-180817 | 7/1999 |
| JP | 2002-308727 | 10/2002 |
| JP | 2007-269723 | 10/2007 |
| JP | 2009-062332 | 3/2009 |
| JP | 2010037348 A * | 2/2010 |
| JP | 2010-235472 | 10/2010 |
| JP | 2011-057567 | 3/2011 |
| JP | 2012-193139 | 10/2012 |
| JP | 2013-136546 | 7/2013 |
| JP | 2017-048181 | 3/2017 |
| JP | 2017-099364 | 6/2017 |
| JP | 2018-511623 | 4/2018 |
| JP | 2018-154837 | 10/2018 |
| KR | 20110112443 A | 10/2011 |
| KR | 2017-0103628 | 9/2017 |
| WO | 2014/088072 | 6/2014 |
| WO | 2017/150950 | 9/2017 |
| WO | WO-2018230600 A1 * | 12/2018 ............. C08B 1/003 |

OTHER PUBLICATIONS

K. Abe and H. Yano. Cellulose nanofiber-based hydrogels with high mechanical strength. Cellulose (2012) 19:1907-1912 (Year: 2012).*
Machine Translation of JP-2010037348-A from EPO. (Year: 2023).*
The International Search Report for PCT/JP2019/050767, dated Mar. 17, 2020.
Office Action for Korean Patent Application No. 10-2021-7013173, dated Jun. 23, 2025.

* cited by examiner

*Primary Examiner* — Michael P Cohen
(74) *Attorney, Agent, or Firm* — Andrus Intellectual Property Law, LLP (57) ABSTRACT

Cosmetics that impart physical resilience and visually smooth-textured appearance to skin, by forming a non-sticky, flexible, and rupture-free makeup film on skin. The solution to the problem is a cosmetic containing cellulose nanofibers having an average fiber diameter of 10 to 1000 nm, in addition to a thickening stabilizer.

18 Claims, 6 Drawing Sheets

COSMETIC

CROSS-REFERENCE TO RELATED APPLICATIONS

This application is the U.S. national stage application of International Application PCT/JP2019/050767, filed Dec. 25, 2019, which international application was published on Jul. 2, 2020, as International Publication WO 2020/138144 in the Japanese language. The International Application claims priority of Japanese Patent Application No. 2018-245915, filed Dec. 27, 2018. The international application and Japanese application are both incorporated herein by reference, in entirety.

TECHNICAL FIELD

The present invention relates to cosmetics.

BACKGROUND ART

A number of cosmetics are on the market, advertised as effective for skin resilience or antiwrinkle. Known approaches for improving skin resilience or elasticity include addition of plant extracts and use of vitamin A derivatives. These approaches, however, scarcely give immediate results, so that it is hard to encourage continuous application over time until the onset of pharmacological effects. In this regard, various attempts have been made, such as physical impartment of resilience by forming a makeup film over the skin to realize instantaneous effect, or minimization of appearance of irregularities like wrinkles to impart visual resilience or glow.

Patent Literature 1 (JP 2007-269723 A) discloses cosmetics containing a water-soluble film-forming agent, such as polyvinyl alcohol, a water-soluble moisturizing agent, and a particular ester oil, and having good spreadability upon application, and imparting good glow and skin resilience. Patent Literature 2 (JP 2010-235472 A) discloses that emulsion cosmetics forming a soft film and excellent in imparting adequate skin resilience are obtained by combination of a solid oil stearyl stearate and a hydrocarbon. Patent Literature 3 (JP 2013-136546 A) teaches that quick-acting skin resilience may be imparted by combined use of an oil-soluble film-forming agent and a highly volatile oily material.

However, the water-soluble polymers, solid oil, and oil-soluble film-forming agent used in these applications, which contribute to impartment of skin resilience by forming a makeup film, cause sticky texture during and after application to skin. In addition, when the resulting makeup film lacks flexibility, the makeup film may rupture due to skin movement. Patent Literature 4 (JP H11-180817 A) discloses a skin resilience-imparting agent that makes skin visually glowing and resilient by means of a powder bright in both specular and diffusing lights, but this agent does not impart physical skin resilience provided by a makeup film.

On the other hand, use of cellulose nanofibers has been discussed, such as for improving strength of composite materials. In the art of cosmetics, however, only the use as a thickener (Patent Literature 5 (JP 2009-62332 A)) or a dispersion stabilizer (Patent Literature 6 (JP 2011-57567 A)) has been discussed, and cellulose nanofibers have never been used for improving properties of a makeup film.

CITATION LIST

Patent Literature

Patent Literature 1: JP 2007-269723 A
Patent Literature 2: JP 2010-235472 A
Patent Literature 3: JP 2013-136546 A
Patent Literature 4: JP H11-180817 A
Patent Literature 5: JP 2009-62332 A
Patent Literature 6: JP 2011-57567 A

SUMMARY OF INVENTION

Technical Problem

The present invention has been made based on these background art. It is an object of the present invention to provide cosmetics that impart physical resilience to skin and provide skin with visually smooth-textured appearance by forming a non-sticky, flexible, and rupture-free makeup film on skin.

Solution to Problem

The present inventors have made intensive studies to find out that cosmetics containing particular cellulose nanofibers solve the problems. The present invention solving the problems are as follows.
(Means Recited in Claim 1)
A cosmetic including cellulose nanofibers having an average fiber diameter of 10 to 1000 nm, in addition to a thickening stabilizer.
(Means Recited in Claim 2)
The cosmetic according to claim 1, wherein a variation coefficient of fiber diameter distribution of the cellulose nanofibers is 1.1 or less.
(Means Recited in Claim 3)
The cosmetic according to claim 1 or 2, wherein a peak value of a pseudo particle size distribution curve of the cellulose nanofibers is 1 to 100 μm, and an accumulated volume fraction of nanofibers having a particle size of 100 μm or smaller of the cellulose nanofibers is 90% or more.
(Means Recited in Claim 4)
The cosmetic according to any one of claims 1 to 3 including 0.01 to 3 mass % of the cellulose nanofibers, and an oil component at 1 to 50 mass %.
(Means Recited in Claim 5)
The cosmetic according to any one of claims 1 to 4, wherein the cosmetic is a base makeup cosmetic.

Effect of the Invention

According to the present invention, the cosmetics are provided which impart physical resilience to skin and provide skin with visually smooth-textured appearance.

DESCRIPTION OF EMBODIMENT

An embodiment for carrying out the invention is now discussed. Note that the present embodiment is an example of the present invention, and the scope of the present invention is not limited to the scope of the present embodiment.

The cosmetic of the present embodiment contains at least particular cellulose nanofibers, in addition to a thickening stabilizer. In some prior art, cellulose nanofibers have been used as a thickening stabilizer. In contrast, according to the present embodiment, cellulose nanofibers are used as, for example, a film-forming component. In other words, according to the present embodiment, the thickening stabilizer is contained as another component, and the conventionally-used cellulose nanofibers fall under (correspond to) such a thickening stabilizer in the present embodiment.

It should be noted that, as will be discussed in detail below, not all the cellulose nanofibers usable as a thickening stabilizer can be used as a film-forming component, and prescribed conditions are applied. Further, in this embodiment, cellulose nanofibers are not used as a thickening stabilizer, but use of cellulose nanofibers as another component thickening stabilizer is not denied.

(Cellulose Nanofibers)

In the present embodiment, particular cellulose nanofibers (CNF) function as a film-forming component. Since the particular cellulose nanofibers are also a kind of cellulose nanofibers, those have a function to suppress sticky texture. Further, the cellulose nanofibers, after application to the skin, function to form a makeup film on the skin together with other non-volatile components in the cosmetics, to thereby impart physical resilience to the skin and provide skin with also visually smooth-textured appearance.

The particular cellulose nanofibers in the present embodiment may be obtained by defibrating (making finer) raw material pulp.

As the raw material pulp for the cellulose nanofibers, it is possible to use for example, one or more members selected from the group consisting of wood pulp made from hardwood, softwood, or the like; non-wood pulp made from straw, bagasse, cotton, hemp, bast fibers, or the like; and de-inked pulp (DIP) made from recovered used paper, waste paper, or the like.

In this regard, however, it is preferred to use wood pulp rather than non-wood pulp or de-inked pulp, as contamination of impurities may be avoided as much as possible and a higher content of α-cellulose may be obtained, which is, among cellulose components, insoluble in alkali. Treatment with alkali removes the components soluble in alkali and improves the purity of cellulose.

As the wood pulp, it is possible to use, for example, one or more members selected from the group consisting of chemical pulp, such as hardwood kraft pulp (LKP) and softwood kraft pulp (NKP), and mechanical pulp (TMP).

The hardwood kraft pulp may be hardwood bleached kraft pulp, hardwood unbleached kraft pulp, or hardwood semi-bleached kraft pulp. Similarly, the softwood kraft pulp may be softwood bleached kraft pulp, softwood unbleached kraft pulp, or softwood semi-bleached kraft pulp.

As the mechanical pulp, it is possible to use, for example, one or more members selected from the group consisting of stone ground pulp (SGP), pressure stone ground pulp (PGW), refiner ground pulp (RGP), chemi-ground pulp (CGP), thermo-ground pulp (TGP), ground pulp (GP), thermomechanical pulp (TMP), chemithermomechanical pulp (CTMP), refiner mechanical pulp (RMP), and bleached thermomechanical pulp (BTMP). It should be noted, however, that for avoiding contamination of impurities other than cellulose as mentioned above, use of chemical pulp, particularly hardwood kraft pulp (LKP) or softwood kraft pulp (NKP), is preferred.

Prior to the defibration into the cellulose nanofibers, pretreatment may be performed by a chemical method. Such pretreatment by a chemical method may be, for example, hydrolysis of polysaccharides with acid (acid treatment), hydrolysis of polysaccharides with enzyme (enzyme treatment), swelling of polysaccharides with alkali (alkali treatment), oxidation of polysaccharides with an oxidizing agent (oxidation treatment), or reduction of polysaccharides with a reducing agent (reduction treatment).

An alkali treatment prior to the defibration causes partial dissociation of hydroxyl groups in hemicellulose or cellulose in pulp, resulting in anionization of the molecules, which weakens intra- and intermolecular hydrogen bonds to promote dispersion of cellulose fibers during the defibration.

As the alkali used in the alkali treatment, it is possible to use, for example, sodium hydroxide, lithium hydroxide, potassium hydroxide, an aqueous ammonia solution, and organic alkali, such as tetramethylammonium hydroxide, tetraethylammonium hydroxide, tetrabutylammonium hydroxide, and benzyltrimethylammonium hydroxide. In view of the manufacturing cost, sodium hydroxide is preferably used.

The enzyme treatment, acid treatment, or oxidation treatment prior to the defibration may result in low water retention, high degree of crystallinity, and also high homogeneity of the cellulose nanofibers. In this regard, cellulose nanofibers at a low water retention are easily dewatered, so that dewaterability of a dispersion of the cellulose nanofibers (sometimes referred to as "slurry" hereinbelow) may be improved.

The enzyme treatment, acid treatment, or oxidation treatment of the raw material pulp causes decomposition of the amorphous region of hemicellulose and cellulose in the pulp, which leads to reduction of energy required for the treatment to make the raw material finer and improvement in uniformity and dispersibility of the cellulose fibers. The dispersibility of the cellulose fibers serves, for example, improvement in homogeneity of the cellulose nanofibers. In the art of cosmetics, content of cellulose nanofibers is small with respect to the total amount of a cosmetic, so that the improvement in homogeneity is an important factor. The pretreatment, however, lowers the aspect ratio of cellulose nanofibers, and it is thus preferred to avoid excessive pretreatment, particularly of the cellulose nanofibers to be used as a film-forming component.

The defibration of the raw material pulp may be effected by beating the raw material pulp in, for example, beaters, homogenizers, such as high-pressure homogenizers and high-pressure homogenizing apparatus, stone mill-type friction machines, such as grinders and grinding machines, single-screw kneaders, multi-screw kneaders, kneaders, refiners, and jet mills. It is preferred to use refiners or jet mills.

The defibration of the raw material pulp is preferably effected so that the average fiber diameter, average fiber length, water retention, degree of crystallinity, variation coefficient of fiber diameter distribution, and peak value of a pseudo particle size distribution curve of the resulting cellulose nanofibers, the pulp viscosity, and the B-type viscosity of the dispersion (slurry) fall under the desired values or evaluations to be discussed below.

The average fiber diameter (average fiber width, or average of diameters of single fibers) of the cellulose nanofibers is preferably 10 to 1000 nm, more preferably 10 to 100 nm, particularly preferably 10 to 80 nm. With an average fiber diameter of the cellulose nanofibers below 10 nm, the function of the cellulose nanofibers as the film-forming component may be impaired. That is, the flexibility of the makeup film formed on the skin may be poor, and ruptures or fissures of the makeup film may occur due to movement of the skin after application. Further, with an average fiber diameter of the cellulose nanofibers below 10 nm, the viscosity of the cosmetics is high, which may cause problems such as lowered spreadability of the cosmetics, or incapability of the desired amount of cellulose nanofibers being contained in the cosmetics. Also, with an average fiber diameter of the cellulose nanofibers below 10 nm, the dewaterability of the slurry containing the cellulose nanofibers may be impaired.

On the other hand, with an average fiber diameter of the cellulose nanofibers above 1000 nm, rough or sticky texture may be imparted to the cosmetics, or the skin resilience may be impaired. In view of the sticky texture and skin resilience, particularly the average fiber diameter of the cellulose nanofibers is preferably 100 nm or smaller.

The average fiber diameter of the cellulose nanofibers may be adjusted by, for example, selection, pretreatment, or defibration of the raw material pulp.

The average fiber diameter of cellulose nanofibers may be determined by the following process.

First, 100 ml of an aqueous dispersion (slurry) of cellulose nanofibers having a solid concentration of 0.01 to 0.1 mass % is filtered through a TEFLON (registered trademark) membrane filter, and subjected to solvent substitution once with 100 ml of ethanol and three times with 20 ml of t-butanol. Then the resulting mass is lyophilized and coated with osmium to obtain a sample. An electron microscopic SEM image of this sample is observed at a magnification of 3000 to 30000 folds, depending on the width of the constituent fibers. Specifically, two diagonal lines are drawn on the observation image, and three arbitrary straight lines passing the intersection of the diagonals are drawn. Then, the widths of a total of 100 fibers crossing these three straight lines are visually measured. The median diameter of the measured values is taken as the average fiber diameter.

The average fiber length (average of lengths of single fibers) of the cellulose nanofibers is preferably 0.3 to 200 μm, more preferably 0.4 to 200 μm, particularly preferably 0.5 to 200 μm. With an average fiber length below 0.3 μm, the cellulose nanofibers may not function as a film-forming component. Further, with an average fiber length of the cellulose nanofibers below 0.3 μm, the skin resilience may be poor.

On the other hand, with an average fiber length of the cellulose nanofibers above 200 μm, the fibers may easily entangle with each other to cause aggregation problem. Note that aggregation of cellulose nanofibers may lead to rough texture of the cosmetics and may cause generation of eraser-like crumbs (creases).

The average fiber length of the cellulose nanofibers may be adjusted by, for example, selection, pretreatment, or defibration of the raw material pulp.

The average fiber length of the cellulose nanofibers may be measured, in the same manner as for the average fiber diameter, by visually measuring the length of each fiber. The median length of the measured values is taken as the average fiber length.

The cellulose nanofibers have a variation coefficient of fiber diameter distribution of preferably 0.1 or more and 1.5 or less, more preferably from 0.3 to 1.1 or less. With a variation coefficient of fiber diameter distribution of above 1.1, the fiber diameter distribution is wide, and not only the nanosized cellulose fibers but also microsized cellulose fibers are included, which leads to lowered fluidity of the cosmetics themselves or discomfort like rough texture upon application to the skin. With a variation coefficient of 0.3 or less, the nanosized fiber diameters tend to be uniform, but the adjustment by the pretreatment or defibration may likely be difficult.

The variation coefficient of the fiber diameter distribution is a value obtained from the average fiber diameter determined by calculating as discussed above and a standard deviation, i.e., the standard deviation/the average fiber diameter.

The water retention of the cellulose nanofibers is preferably 500% or lower, more preferably 300 to 480%. With a water retention of the cellulose nanofibers below 300%, the dispersibility of the cellulose nanofibers may be impaired. Further, with a water retention of the cellulose nanofibers below 300%, rough texture of the cosmetics may result.

On the other hand, with a water retention of the cellulose nanofibers above 500%, the water retention of the cellulose nanofibers themselves is too high, and the dewaterability of the cellulose nanofibers may be impaired.

The water retention of the cellulose nanofibers may be adjusted by, for example, selection, pretreatment, or defibration of the raw material pulp.

The water retention of the cellulose nanofibers is a value determined in compliance with JAPAN TAPPI No. 26: 2000.

The pulp viscosity of the cellulose nanofibers is preferably 1 to 10 cps, more preferably 2 to 9 cps, particularly preferably 3 to 8 cps. The pulp viscosity is a viscosity of a solution of cellulose dissolved in a copper-ethylenediamine solution, and a higher pulp viscosity indicates higher degree of polymerization of cellulose. The pulp viscosity is associated with strength and rigidity of cellulose fibers. With too high a polymerization degree, the skin resilience may be poor and the affinity to the skin may likely be impaired, whereas with too low a polymerization degree, the strength of the fibers themselves may be lost, and the film may be prone to fissuring. The polymerization degree of the cellulose nanofibers may be adjusted by, for example, selection, pretreatment, or defibration of the raw material pulp. With a pulp viscosity within the above-mentioned range, the cellulose nanofibers may function as the film-forming component, while the occurrence of rough texture may be prevented.

The peak value of a pseudo particle size distribution curve of the cellulose nanofibers (sometimes referred simply to "peak value" hereinbelow) is preferably of one peak. With one peak, the cellulose nanofibers have high uniformity in fiber length and fiber diameter, and are suitable for use as a raw material of cosmetics.

The peak value of the cellulose nanofibers is, for example, 1 to 100 μm, preferably 3 to 80 μm, more preferably 5 to 60 μm. A peak value of the cellulose nanofibers below 1 μm indicates progress of size reduction of cellulose, whereas a peak value of the cellulose nanofibers above 100 μm may indicate that the fibers are not defibrated into the nanosize.

The peak value of the cellulose nanofibers may be adjusted by, for example, selection, pretreatment, or defibration of the raw material pulp.

The peak value of the cellulose nanofibers is a value determined in compliance with ISO-13320 (2009). More specifically, first, a volume-based particle size distribution of an aqueous dispersion of the cellulose nanofibers is determined using a particle size distribution measuring apparatus (a laser diffraction/scattering-type particle size distribution measuring apparatus manufactured by SEISHIN ENTERPRISE CO., LTD.). Then the median diameter of the cellulose nanofibers is determined from this distribution, and this median diameter is taken as the peak value.

In addition to the peak value discussed above, the cellulose nanofibers have an accumulated volume fraction of the fibers having a particle size of 100 μm or smaller, preferably 70% or more, more preferably 90% or more. With an accumulated volume fraction of the fibers having a particle size of 100 μm or smaller of less than 70%, for example, as will be anticipated from the test examples to be discussed later, the sticky texture may be imparted, the skin resilience may be impaired, and the function as the film-forming component may not be fulfilled.

The cellulose nanofibers obtained by the defibration may be kept in the form of a dispersion (slurry), as needed, prepared by dispersion in an aqueous medium. It is particularly preferred that the aqueous medium is entirely water (aqueous solution). However, part of the aqueous medium may be another liquid compatible with water. Such another liquid may be, for example, lower alcohols having 3 or less carbon atoms.

The B-type viscosity of the dispersion of the cellulose nanofibers (1.5% concentration) is preferably 1000 cps to 20000 cps, more preferably 1000 to 10000 cps, particularly preferably 1000 to 5000 cps. With the B-type viscosity of the dispersion within the above range, mixing with the other components of the cosmetics may be facilitated, and the dewaterability of the slurry (dispersion) may be improved.

The B-type viscosity of the dispersion of the cellulose nanofibers (1.5% solid content) is a value determined in compliance with JIS-Z8803: 2011 "Method for viscosity measurement of liquid". A B-type viscosity is a resistant torque in stirring a dispersion, and a higher value indicates more energy required for stirring.

It is preferred to adjust the solid content of the cellulose nanofibers in the dispersion of the cellulose nanofibers by, for example, adding a solvent such as water. The solid content of the cellulose nanofibers is preferably 0.1% to 5.0%, more preferably 0.3 to 4.0%, particularly preferably 0.5 to 3.0%. With a solid content of the cellulose nanofibers below 0.1%, the fluidity is too high, which may cause difficulties in mixing with the other components. On the other hand, with a solid content of the cellulose nanofibers above 5.0 mass %, the fluidity is remarkably low, which may also cause difficulties in mixing with the other components.

The cellulose nanofibers may be dispersed in either aqueous or oil phase in the cosmetics. Dispersion in an aqueous phase is preferred for its preservation stability and spreadability on the skin of the cosmetics.

The content of the cellulose nanofibers in the cosmetic is preferably 0.01 to 3 mass %, more preferably 0.05 to 2 mass %, particularly preferably 0.1 to 1 mass %. With an excessively low content of the cellulose nanofibers, the skin resilience is poor, and the function as the film-forming component may not be fulfilled. On the other hand, with an excessively high content of the cellulose nanofibers, the spreadability of the cosmetics is poor and the flexibility of the makeup film is low.

(Oil Component)

In the cosmetics of the present embodiment, an oil phase is present as a dispersed phase. The oil component, after being applied to the skin, functions to form a makeup film together with the cellulose nanofibers and the like components to impart resilience to the skin.

The oil component may be, for example, of any origin, such as animal, vegetable, or synthetic oil, or in any state, such as solid, semi-solid, liquid, or volatile oil.

The oil component may be, for example, one or a combination of two or more members selected from the group consisting of hydrocarbons, oils and fats, waxes, hydrogenated oils, ester oils, fatty acids, silicone oils, fluorine oils, lanolin derivatives, and oil-soluble UV absorbers.

More specifically, for example, one or a combination of two or more members may be used, selected from the group consisting of: hydrocarbons, such as liquid paraffin, squalene, petrolatum, paraffin wax, ceresin wax, microcrystalline wax, Japan wax, and montan wax;

oils and fats, such as olive oil, castor oil, jojoba oil, mink oil, and macadamia nut oil;

waxes, such as beeswax, lanolin, carnauba wax, candelilla wax, and spermaceti;

esters, such as cetylisooctanate, isopropyl myristate, isopropyl palmitate, octyldodecyl myristate, glyceryl trioctanoate, glyceryl tribehenate, rosin pentaerythritol ester, and neopentyl glycol dioctanoate;

silicones, such as low polymer dimethylpolysiloxane, high polymer dimethylpolysiloxane, methylphenylpolysiloxane, decamethylcyclopentasiloxane, octamethylcyclotetrasiloxane, and fluorine-modified silicones;

fluorine oils, such as perfluoropolyether, perfluorodecane, and perfluorooctane; and lanolin derivatives, such as lanolin, acetylated lanolin, lanolin fatty acid isopropyl esters, and lanolin alcohols.

The content of the oil component in the cosmetic is preferably 1 to 50 mass %, more preferably 3 to 40 mass %, particularly preferably 5 to 25 mass %. With a content of the oil component below 1 mass %, the flexibility of the makeup film may be poor. On the other hand, with a content of the oil component above 50 mass %, the skin resilience may be lowered and the sticky texture may not be removed.

(Powder)

In the cosmetics according to the present embodiment, powder may be contained. With powder contained in the cosmetics, the sticky texture of a makeup film may further be suppressed. Further, in the use of the cosmetics according to the present embodiment as base makeup cosmetics, desired covering ability and finish may be obtained.

The powder is not limited by, for example, its shape, such as spherical, plate, spindle, or needle shape, its particle size, or its particle structure, such as porous or non-porous structure. The powder may also be any of inorganic powder, glittering powder, organic powder, pigments, and compound powder.

As the powder, one or a combination of two or more members may be used, selected from the group consisting of: inorganic powders, such as titanium oxide, zinc oxide, zirconium oxide, cerium oxide, red iron oxide, yellow iron oxide, black iron oxide, iron blue, ultramarine, silicic anhydride, magnesium carbonate, calcium carbonate, aluminum hydroxide, chromium hydroxide, carbon black, aluminum silicate, magnesium silicate, magnesium aluminum silicate, mica, smectite, bentonite, kaolin, synthesized mica, synthesized sericite, sericite, talc, silicon carbide, barium sulfate, and boron nitride;

photoluminescent powders, such as bismuth oxychloride, titanium dioxide-coated mica, iron oxide-coated mica, iron oxide-coated titanium dioxide-coated mica, organic pigment-coated titanium dioxide-coated mica, and aluminum powder; and organic powders, such as magnesium stearate, zinc stearate, N-acyllysine, polystyrene, nylon, polymethylmethacrylate, polymethylsilsesquioxane powder, organopolysiloxane elastomer powder, cellulose, crystalline cellulose, and cellulose acetate.

The powders mentioned above may be subjected to surface treatment before use, as required, with a surface treatment agent, such as inorganic compounds, for example, alumina, silica, or iron oxide, fluorine compounds, silicone compounds, phospholipids, phospholipid derivatives, metal soaps, waxes, surfactants, oils and fats, or hydrocarbons.

Among the abovementioned, use of spherical organic powders, for example, polystyrene, nylon, polymethylmethacrylate, polymethylsilsesquioxane powder, organopolysiloxane elastomer powder, cellulose, crystalline cellulose, or cellulose acetate may effectively conceal the irregularities, such as pores and fine wrinkles, to provide favorable finish.

In using the cosmetics of the present embodiment as base makeup cosmetics, it is preferred to use, as the powder, one or a combination of two or more inorganic powders, such as titanium oxide, red iron oxide, yellow iron oxide, and black iron oxide. In particular, inorganic powders coated with metal oxide such as silica disperse well in the aqueous phase or the continuous phase, and are thus excellent in emulsion stability and prevention of color change.

As an example of a commercially available silica-coated red iron oxide, SYMPHOLIGHT RW (manufactured by JGC CATALYSTS AND CHEMICALS LTD.) may be used. As an example of a commercially available silica-coated yellow iron oxide, SYMPHOLIGHT Y10 may be used.

The content of the powder is preferably 1 to 40 mass %, more preferably 3 to 30 mass %, particularly preferably 5 to 25 mass %, based on the total amount of the cosmetic. With a powder content of less than 1 mass %, the makeup film may tend to be sticky. On the other hand, with a content of the powder cosmetic above 40 mass %, the flexibility of the makeup film may be poor.

(UV Protector)

As used herein, a UV protector means a component that protects skin or cosmetics per se against ultraviolet (UV) rays by absorbing UV rays (UV absorber) or scattering UV rays (UV scattering agent). In this regard, it is said that UV scattering agents generally used in cosmetics are capable of also absorbing UV rays. In the present embodiment, it is not necessary to clearly distinguish between the UV absorbers and the UV scatting agents, and either of them are used to protect skin or the cosmetics per se against UV rays. Herein, both UV absorbers and UV scattering agents are defined as being included in the UV protectors.

The UV absorbers include water-soluble UV absorbers, and oil-soluble UV absorbers, which fall under the category of oil components. The water-soluble UV absorbers may be, for example, one or a combination of two or more members selected from the group consisting of: benzophenone-based UV absorbers, such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone; benzimidazole-based UV absorbers, such as phenylbenzimidazole-5-sulfonic acid and salts thereof, and phenylene-bis-benzimidazole tetrasulfonic acid and salts thereof; and 3-(4'-methylbenzylidene)-d,l-camphor, 3-benzylidene-d,l-camphor, urocanic acid, and urocanic acid ethyl ether.

The oil-soluble UV absorbers may be, for example, one or a combination of two or more members selected from the group consisting of: cinnamate-based UV absorbers, such as benzyl p-methoxycinnamate, 2-ethylhexyl p-methoxycinnamate, and glyceryl mono-2-ethylhexanoate di-p-methoxycinnamate; benzophenone-based UV absorbers, such as hydroxymethoxybenzophenone, dihydroxymethoxybenzophenone, dihydroxybenzophenone, and tetrahydroxybenzophenone; benzoate-based UV absorbers, such as p-aminobenzoic acid, ethyl p-aminobenzoate, glyceryl p-aminobenzoate, amyl p-dimethylaminobenzoate, octyl p-dimethylaminobenzoate, ethyl 4-[N,N-di(2-hydroxypropyl)amino] benzoate, and hexyl diethylaminohydroxybenzoylbenzoate;

salicylate-based UV absorbers, such as ethylene glycol salicylate, phenyl salicylate, octyl salicylate, benzyl salicylate, p-tert-buthylphenyl salicylate, and homomenthyl salicylate;

triazine-based UV absorbers, such as ethylhexyl triazone (2,4,6-tris[4-(2-ethylhexyloxycarbonyl)anilino]-1,3,5-triazine and bis-ethylhexyloxyphenol methoxyphenyl triazine; and 4-tert-butyl-4'-methoxybenzoylmethane, menthyl anthranilate, 2-(2-hydroxy-5-methylphenyl)benzotriazole, 2-ethylhexyl dimethoxybenzylidene dioxoimidazolidine propionate, octocrylene, and dimethicodiethylbenzal malonate.

The UV scattering agents are in the form of fine particle powders, and fall under the category of the above-mentioned powder. The UV scattering agents are preferably in the form of metal oxide having an average particle size of 100 nm or smaller. Specifically, for example, one or a combination of two or more members may be used, selected from the group consisting of titanium oxide, zinc oxide, and cerium oxide, all having an average particle size of 100 nm or smaller.

The UV scattering agents are preferably those having been subjected to hydrophobic treatment in view of waterproofness. The hydrophobic treatment may be performed by an ordinary surface treatment. Specifically, for example, oils and fats treatment by which the powders are lipophilized by causing oils and fats to be adsorbed on the powder surface, or by esterification or etherification using the functional groups, such as hydroxyl groups; metal soap treatment using zinc, magnesium, or aluminum salts of fatty acid; silicone treatment using a silicone compound, such as dimethylsiloxane or hydrogen dimethicone; treatment with a fluorine compound having a perfluoroalkyl group; or treatment with alkylalkoxysilane, may be adopted. Among the treatments mentioned above, silicone treatment using a silicone compound is preferred for waterproofness and emulsion stability.

The content of the UV protector is preferably 1 to 40 mass %, more preferably 3 to 30 mass %, particularly preferably 5 to 25 mass %, based on the total amount of the cosmetic. With a content of the UV protector of less than 1 mass %, the UV protective effect is insufficient. On the other hand, with a content of the UV protector of above 40 mass %, the spreadability of the cosmetic on the skin may be impaired.

(Film Component)

The cosmetics according to the present embodiment include oil-in-water emulsion cosmetics, and preferably contain one or more kinds of film components selected from the group consisting of water-soluble film-forming agents, oil-soluble film-forming agents, and film-forming polymer emulsion. With such a film-component, resilience of the skin may further be improved.

The water-soluble film-forming agent dissolves in an aqueous component to form a makeup film. The water-soluble film-forming agent may be, for example, one or a combination of two or more members selected from the group consisting of polyvinylpyrrolidone, polyvinyl alcohol, polyethylene glycol, vinyl acetate, vinylpyrrolidone copolymers, modified corn starch, and hydrogenated starch hydrolysate.

The oil-soluble film-forming agent dissolves or disperses in an oil component to form a makeup film. The oil-soluble film-forming agent may be, for example, one or a combination of two or more members selected from the group consisting of: silicone-based resins, such as trimethylsiloxysilicate, partially cross-linked organopolysiloxane, trimethylsiloxy silylpropyl carbamate, fluorine-modified silicone, acrylic modified silicone, and silicone dendrimer-modified resin compounds; rosin acid-based resins, such as pentaerythrityl rosinate, and glyceryl rosinate; candelilla resin, polyvinyl acetate-based resins, polyvinyl isobutyl ether, and polyisobutylene.

Among these, partially cross-linked organopolysiloxane is particularly preferred for its ability to form a waterproof makeup film with little sticky texture. The partially cross-linked organopolysiloxane is available in the form of a gel dispersed in liquid oil. Examples of a commercially available product of partially cross-linked organopolysiloxane include KSG-15, which is composed of (dimethicone/vinyl dimethicone) crosspolymer and cyclopentasiloxane, KSG-1510, which is composed of (dimethicone/vinyl dimethicone) crosspolymer and methyltrimethicone, KSG-16, which is composed of (dimethicone/vinyl dimethicone) crosspolymer and dimethicone, KSG-18A, which is composed of (dimethicone/phenyl vinyl dimethicone) crosspolymer and diphenylsiloxy phenyl trimethicone, KSG-41A, which is composed of (vinyl dimethicone/lauryl dimethicone) crosspolymer and liquid paraffin, KSG-43, which is composed of (vinyl dimethicone/lauryl dimethicone) crosspolymer and triethylhexanoin, and KSG-042Z, which is composed of (laurylpolydimethylsiloxyethyl dimethicone/bis-vinyldimethicone) crosspolymer and isododecane, all manufactured by SHIN-ETSU CHEMICAL CO., LTD.; 9040 and 9045 Silicone Elastomer Blend, which are composed of dimethicone crosspolymer and cyclopentasiloxane, 9041 Silicone Elastomer Blend, which is composed of dimethicone crosspolymer and dimethicone, 3901 Liquid Satin Blend, which is composed of (dimethicone/vinyl dimethicone) crosspolymer and dimethicone, and EL-8051 IN Silicone Organic Elastomer Blend, which is composed of (dimethicone/bis-isobutyl PPG-20) crosspolymer and isodecyl neopentanoate, all manufactured by DOW CORNING TORAY CO., LTD.; Velvesil 125, which is composed of alkyl(C30-45) cetearyl dimethicone crosspolymer and cyclopentasiloxane, Velvesil 034, which is composed of alkyl(C30-45) cetearyl dimethicone crosspolymer and caprylyl methicone, and Velvesil DM, which is composed of cetearyl dimethicone crosspolymer and dimethicone, all manufactured by MOMENTIVE PERFORMANCE MATERIALS.

The film-forming polymer emulsion is an aqueous dispersion of a water-insoluble polymer. The film-forming polymer emulsion may be, for example, one or a combination of two or more members selected from the group consisting of alkyl acrylate copolymer emulsion, alkyl methacrylate copolymer emulsion, styrene-alkyl acrylate copolymer emulsion, styrene-alkyl methacrylate copolymer emulsion, vinyl acetate polymer emulsion, vinyl pyrrolidone-styrene copolymer emulsion, alkyl acrylate-vinyl acetate copolymer emulsion, alkyl methacrylate-vinyl acetate copolymer emulsion, acrylic acid-alkyl acrylate copolymer emulsion, acrylic acid-alkyl methacrylate copolymer emulsion, methacrylic acid-alkyl acrylate copolymer emulsion, methacrylic acid-alkyl methacrylate copolymer emulsion, and alkyl acrylate-dimethicone copolymer emulsion.

The content of the film component is preferably 0.01 to 10 mass %, more preferably 0.1 to 5 mass %, based on the total amount of the cosmetic. With too low a content of the film component, enhancing effect on the skin resilience may not be obtained. On the other hand, with too high a content of the film component, the sticky texture may not be suppressed.

(Thickening Stabilizer)

The cosmetics according to the present embodiment contain a thickening stabilizer that functions as at least either of a thickener and a stabilizer. With this component, sensation in use, such as spreadability of the cosmetics may be improved, and the state of emulsion or dispersion may be maintained for a prolonged period of time. The thickening stabilizer may be, for example, water-soluble polymers other than the water-soluble film-forming agents, or clay minerals.

More specifically, the thickening stabilizer may be, for example, one or a combination of two or more members selected from the group consisting of carboxyvinyl polymers, sodium polyacrylate, acrylic acid-alkyl methacrylate copolymers, (PEG-240/decyltetradeceth-20/HDI) copolymers, (sodium acrylate/acryloyldimethyltaurate) copolymers, (hydroxyethyl acrylate/sodium acryloyldimethyl taurate) copolymers, (ammonium acryloyldimethyltaurate/VP) copolymers, (ammonium acryloyldimethyltaurate/beheneth-25 methacrylate) crosspolymers, (alkylacrylate/steareth-20 methacrylate) copolymers, (dimethylacrylamide/sodium acryloyldimethyl taurate) crosspolymers, polyacrylamide, polyoxyethylene-polyoxypropylene block copolymers, polyvinylmethyl ether, methyl cellulose, ethyl cellulose, hydroxyethyl cellulose, hydroxypropyl cellulose, hydroxypropylmethyl cellulose, sodium carboxymethyl cellulose, cationized cellulose, sodium alginate, propylene glycol alginate, guar gum, locust bean gum, gum arabic, tragacanth, galactan, carob gum, karaya gum, pectin, agar, quince seed (*Cydonia oblonga*), algae colloid (brown alga extract), carrageenan, xanthan gum, dextran, pullulan, bentonite, montmorillonite, hectorite, magnesium aluminum silicate, and laponite.

It is preferred, however, to use one or a combination of two or members selected from the group consisting of carboxyvinyl polymers, acrylic acid-alkyl methacrylate copolymers, xanthan gum, (sodium acrylate/acryloyldimethyl taurate) copolymers, and hydroxypropylmethyl cellulose.

The content of the thickening stabilizer is preferably 0.01 to 5 mass %, more preferably 0.02 to 4 mass %, particularly preferably 0.05 to 3 mass %, based on the total amount of the cosmetic. With a content of the thickening stabilizer below 0.01 mass %, improvement in sensation in use and stabilization of the emulsion/dispersion state may not be achieved. Cellulose nanofibers are conventionally used as a thickening stabilizer, but in the present embodiment, cellulose nanofibers are used as a film-forming component. According to the present embodiment, cellulose nanofibers are added to cosmetics under the prescribed conditions in order to function as a film-forming component, and the above-mentioned thickening stabilizer is separately added to develop the thickening stabilization function.

(Surfactant)

The cosmetic according to the present embodiment may contain a surfactant, such as nonionic surfactants, polymeric emulsifiers, anionic surfactants, cationic surfactants, amphoteric surfactants, or semipolar surfactants. The surfactant may function not only as an emulsifier, but also as, for example, a solubilizer, moisturizer, or detergent.

The anionic surfactant may be, for example, carboxylates, such as fatty acid soaps, ether carboxylic acids and salts thereof, and condensates of amino acids and aliphatic acids, alkyl sulfonates, alkene sulfonates, sulfonates of fatty acid esters, sulfonates of fatty acid amides, sulfonates as condensates of alkyl sulfonate and formalin, sulfates, such as alkyl sulfates, secondary higher alcohol sulfates, alkyl and aryl ether sulfates, sulfates of fatty acid esters, sulfates of fatty acid alkylolamides, and Turkey red oil, alkyl phosphates, alkyl ether phosphates, alkyl aryl ether phosphates, and amidophosphates.

The cationic surfactant may be, for example, amine salts, such as alkylamine salts, polyamines, and amino alcohol fatty acid derivatives, alkyl quaternary ammonium salts, aromatic quaternary ammonium salts, pyridinium salts, or imidazolium salts.

The amphoteric surfactant may be, for example, betaine, amino carboxylates, or imidazoline derivatives.

The nonionic surfactant may be, for example, sorbitan fatty acid esters, polyoxyethylene sorbitan fatty acid esters, glycerin fatty acid esters, polyglyceryl fatty acid esters, ethylene oxide derivatives of glycerin fatty acid esters, propylene glycol fatty acid esters, ethylene oxide derivatives of propylene glycol fatty acid esters, polyethylene glycol fatty acid esters, sucrose esters, polyoxyethylene alkyl ethers, polyoxypropylene alkyl ethers, polyoxyethylene alkylphenyl ethers, polyoxyethylene caster oil derivatives, polyoxyethylene hydrogenated caster oil derivatives, polyoxyethylene phytostanol ethers, polyoxyethylene phytosterol ethers, polyoxyethylene cholestanol ethers, polyoxyethylene cholesteryl ethers, or polyoxyalkylene-modified organopolysiloxanes.

(Moisturizer)

The cosmetic according to the present embodiment may contain a moisturizer. The moisturizer may be, for example, one or a combination of two or more members selected from the group consisting of polyhydric alcohols, sugars, sugar alcohols, amino acids, peptides, and water-soluble polymers. Further, the moisturizer may be, for example, xylitol, sorbitol, maltitol, chondroitin sulfate, hyaluronic acid, collagen, sodium lactate, DL-pyrrolidone carboxylate, chestnut rose extract, *Achillea millefolium* extract, or melilot extracts.

(Other Components)

The cosmetic according to the present embodiment may contain various components that are typically contained in cosmetics, such as antimicrobial agents, preservatives, perfumes, antioxidants, pH adjusting agents, chelating agents, algefacients, anti-inflammatory agents, components for improving skin conditions, vitamins, amino acids, nucleic acids, and inclusion compounds.

(Production Method)

For producing the cosmetics of the present embodiment, ordinary production method may be adopted, such as preparation of oil-in-water emulsion by separate preparation of aqueous and oil phases, followed by graduate addition of the oil phase into the aqueous phase under stirring, soap emulsification or reactive emulsification, or D-phase emulsification.

(Use Application)

The cosmetics according to the present embodiment may be in any of cream, gel, emulsion, or liquid (thin emulsion) state. The cosmetics according to the present embodiment are particularly excellent in preparing makeup cosmetics, such as foundations and makeup bases. However, the cosmetics according to the present embodiment are also excellent in preparing makeup cosmetics, such as eye shadows, blushers, or concealers, in emulsion or cream state.

EXAMPLES

Next, various test results are shown below to further explain the effects of the present invention.

The oil-in-water emulsion cosmetics having the compositions shown in Table 1 (samples) were prepared according to the production procedure to be discussed below. Then, each of the samples thus prepared was applied to the skin (face) of evaluation panels and to artificial skin for evaluation made of urethane (manufactured by BEAULAX CO., LTD.), and dried at room temperature for 30 minutes or longer. Each sample was evaluated by the standard to be discussed below.

As the raw material of the cellulose fibers (CNF-A, CNF-B, MFC) contained in the samples, softwood bleached kraft pulp was used. As CNF-C, RHEOCRYSTA, a product of DKS CO., LTD. (TEMPO oxidized CNF) was used. Properties of each cellulose fiber are shown in Table 2. Determination of the average fiber width was made by the method discussed above (observation of SEM image) for CNF-A and CNF-B. For CNF-C, the determination was made using a transmission electron microscope (TEM). For MFC, the determination was made using a fiber image analyzer FS5 manufactured by VALMET. The drying shrinkage was determined according to the following method.

(Drying Shrinkage)

First, the cellulose fibers, such as CNF, were dispersed to prepare an aqueous dispersion, and its concentration was adjusted to 0.5 mass %. Then, 30 g (wet weight) of the aqueous dispersion with the concentration thus adjusted was introduced into a petri dish of 7.5 cm diameter, and dried at 105° C. The cellulose fiber membrane obtained from this drying process was subjected to the measurement of shrinkage of the diameter. The shrinkage was determined by the following formula, following the calculation of the diameter of the cellulose fiber membrane (calculation of the average of the four lines): Shrinkage=Diameter of cellulose fiber membrane/Inner diameter of container (7.5 cm)×100(%).

TABLE 1

| # | Component | Example 1 | Example 2 | Comparative Example 3 | Comparative Example 4 | Comparative Example 5 | Comparative Example 6 | Function |
|---|---|---|---|---|---|---|---|---|
| 1 | Purified water | Balance | Balance | Balance | Balance | Balance | Balance | — |
| 2 | BG | 10 | 10 | 10 | 10 | 10 | 10 | Moisturizer, antimicrobial agent |
| 3 | Phenoxy ethanol | 0.4 | 0.4 | 0.4 | 0.4 | 0.4 | 0.4 | Preservative |

TABLE 1-continued

| # | Component | | Example 1 | Example 2 | Comparative Example 3 | Comparative Example 4 | Comparative Example 5 | Comparative Example 6 | Function |
|---|---|---|---|---|---|---|---|---|---|
| 4 | Xanthan gum | | 0.3 | 0.3 | 0.3 | 0.3 | 0.3 | 0.3 | Thickener, thickening stailizer |
| 5 | Diisostearyl malate | | 3 | 3 | 3 | 3 | 3 | 3 | (Smoothness, Skin emollient effect) |
| 6 | Ethylhexyl palmitate | | 20 | 20 | 20 | 20 | 20 | 20 | (Refreshing feeling) |
| 7 | Coconut fatty acid succose | | 0.4 | 0.4 | 0.4 | 0.4 | 0.4 | 0.4 | Surfactant (emulsifier, detergent) |
| 8 | Sorbitan stearate | | 2.7 | 2.7 | 2.7 | 2.7 | 2.7 | 2.7 | Nonionic surfactant |
| 9 | Hydrogen dimethicone-treated fine particle titanium oxide | | 8 | 8 | 8 | 8 | 8 | 8 | UV scattering agent |
| 10 | (Dimethicone/Vinyldimethicone) crosspolymer, dimethicone*1 | | 2 | 2 | 2 | 2 | 2 | 2 | Oil-soluble film-forming agent |
| 11 | Mixture containing (sodium acrylate/acryloyldimethyl taurate) copolymer *2 | | 0.2 | 0.2 | 0.2 | 0.2 | 0.2 | 0.2 | Thickening stablizer, emulsion stabilizer |
| 12 | Silica-coated titanium oxide | | 7 | 7 | 7 | 7 | 7 | 7 | Colorant |
| 13 | Silica-coated red iron oxide | | 0.2 | 0.2 | 0.2 | 0.2 | 0.2 | 0.2 | Colorant |
| 14 | Silica-coated yellow iron oxide | | 0.5 | 0.5 | 0.5 | 0.5 | 0.5 | 0.5 | Colorant |
| 15 | Silica-coated black iron oxide | | 0.1 | 0.1 | 0.1 | 0.1 | 0.1 | 0.1 | Colorant |
| 16 | PVA | | — | — | — | — | — | — | Film component (skin resilience) |
| 17 | Cellulose fibers | Kind | CNF-A | CNF-B | — | CNF-C | — | MFC | Film-forming component |
| 18 | | Amount | 20 | 20 | 0 | 20 | 20 | 20 | |
| | Total | | 100 | 100 | 100 | 100 | 100 | 100 | — |

*1 Trade name KSG-16 (manufactured by SHIN-ETSU CHEMICAL CO., LTD.)
*2 Trade name SIMULGEL EG (manufactured by SEPPIC)

TABLE 2

| | | Cellulose Fiber | | | |
|---|---|---|---|---|---|
| Kind | | CNF-A | CNF-B | MFC | CNF-C |
| Average Fiber Width | nm | 50.8 | 285.7 | 16,200 | 3~<10 |
| Median diameter | nm | 45.8 | 189.1 | — | |
| Maximum | nm | 125.0 | 1,260.9 | — | |
| Minimum | nm | 25.0 | 21.7 | — | |
| Standard deviation | — | 18.0 | 291.3 | — | |
| Coefficient of variation | — | 0.35 | 1.02 | — | |
| B-type viscosity: 1.5% | cps | 2,120 | 1,350 | 1,220 | 10,000< |
| B-type viscosity: 0.5% | cps | 105 | 76 | 69 | 466 |
| Water retention | cp | 342 | 321 | 308 | Unmeasurable |
| Pulp viscosity | % | 5 | 4 | 6 | Unmeasurable |
| Drying shrinkage | at 0.5% | 84.6% | 82.5% | 76.2% | 70.6% |

(Production Procedure)

Each of the oil-in-water emulsion foundations prescribed as shown in Table 1 was prepared according to the production procedure discussed below, and evaluated as to "lack of sticky texture", "skin resilience", "lack of skin tightness", "smoothness of finish", "film flexibility", and "skin texture scoring based on image analysis". Based on Table 1:

(1) Components of #1 to #4 were mixed at a mixing ratio as shown in Table 1 and heated to 80° C. to dissolve, to thereby prepare aqueous phase (a), (2) Components of #5 to #11 were mixed at a mixing ratio as shown in Table 1 and heated to 80° C. to dissolve, to thereby prepare oil phase (b), (3) The oil phase (b) was added in small portions to the aqueous phase (a) under stirring to prepare emulsion phase (c), (4) The emulsion phase (c) was cooled down to 35° C., to which the components of #12 to #18 were mixed at a mixing ratio as shown in Table 1 to prepare a cosmetic.

(Evaluation: Sensation in Use)

Each sample (Examples 1 and 2 and Comparative Examples 3 to 6) was applied to the faces of female evaluation panels (5 panels), and sensory evaluations were made as to sensation in use (lack of sticky texture, skin resilience, lack of skin tightness, and smoothness of finish) by the standard mentioned below. The results of the lack of sticky texture, skin resilience, and smoothness of finish are shown in Table 3, and the results of lack of skin tightness are shown in Table 4. For each item, the results are evaluated on a scale of 1 to 3, i.e., "good (marked 2)", "do not know (marked 1)", and "bad (marked 0)", and from the average of the marks the properties were judged by the following standard.

| [Judgement] | Average of marks |
|---|---|
| 5 | 1.5 or more |
| 4 | 1.2 or more and less than 1.5 |
| 3 | 0.8 or more and less than 1.2 |
| 2 | 0.3 or more and less than 0.8 |
| 1 | less than 0.3 |

TABLE 3

|  | Example 1 | Example 2 | Comparative Example 3 | Comparative Example 4 | Comparative Example 5 | Comparative Example 6 |
| --- | --- | --- | --- | --- | --- | --- |
| Lack of sticky texture | 5 | 4 | 3 | 5 | 1 | 3 |
| Skin resilience | 4 | 3 | 1 | 5 | 4 | 2 |
| Smoothness of finish | 5 | 4 | 1 | 5 | 2 | 3 |

TABLE 4

|  | Example 1 | Example 2 | Comparative Example 3 | Comparative Example 4 | Comparative Example 5 | Comparative Example 6 |
| --- | --- | --- | --- | --- | --- | --- |
| Lack of skin tightness | 4 | 4 | 5 | 1 | 1 | 5 |
| Film flexibility | 5 | 5 | 5 | 3 | 5 | 5 |
| Skin texture score | 5 | 5 | 1 | 5 | 1 | 3 |

(Film Flexibility)

Figure 1:
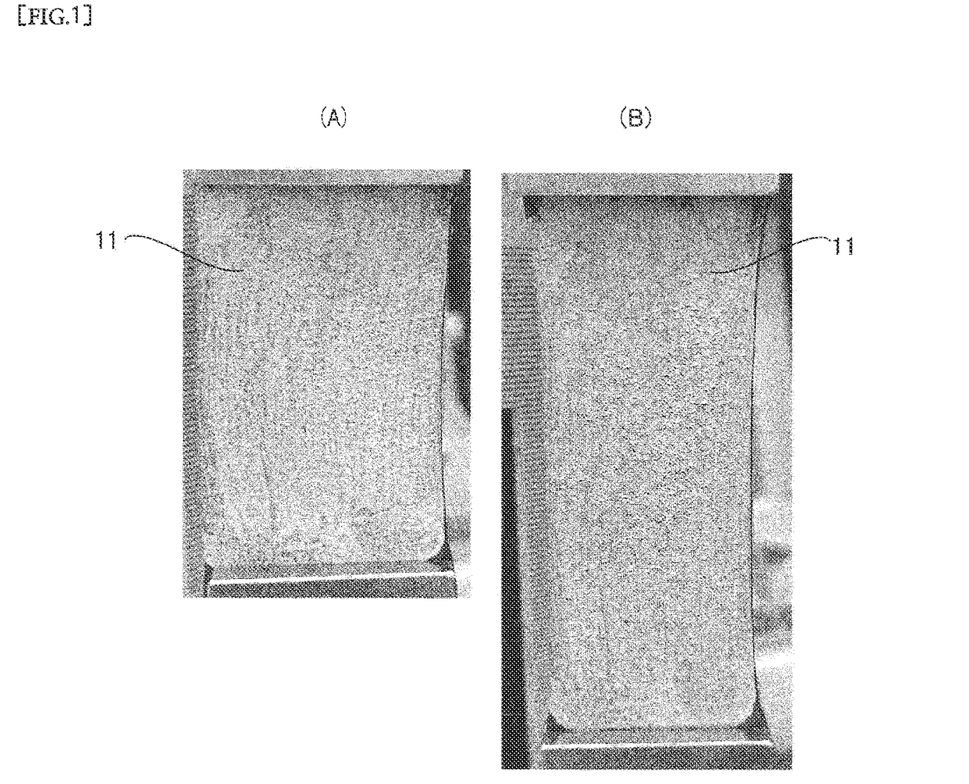
FIG. 1 shows images illustrating the results of the test on film flexibility.
Figure 2:
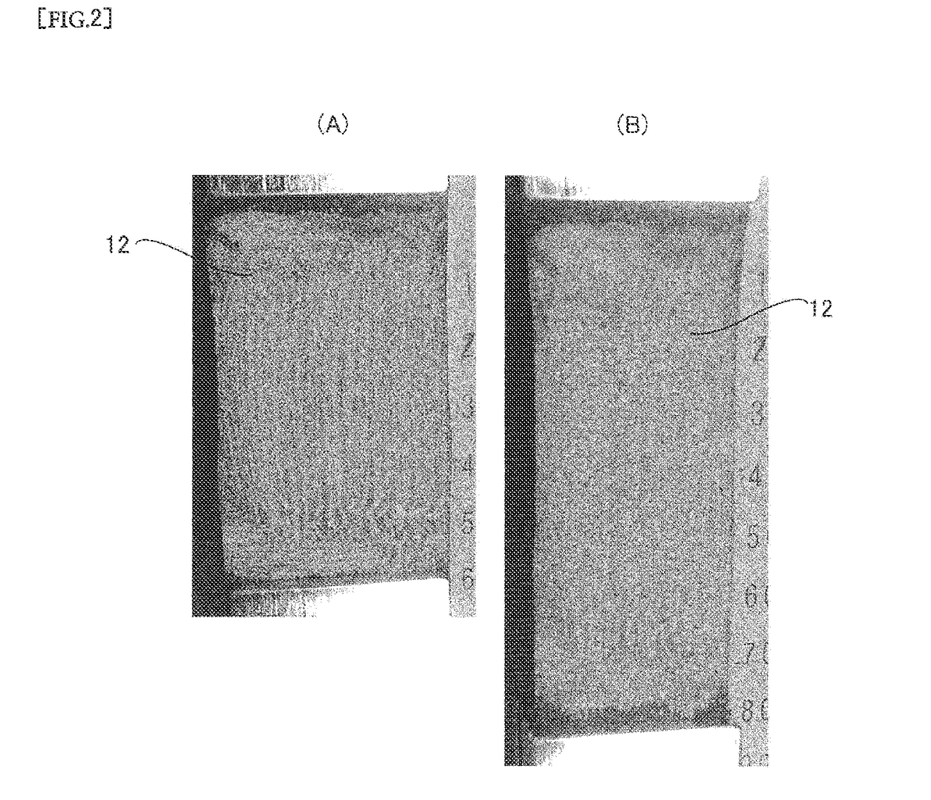
FIG. 2 shows images illustrating the results of the test on film flexibility.
Figure 3:
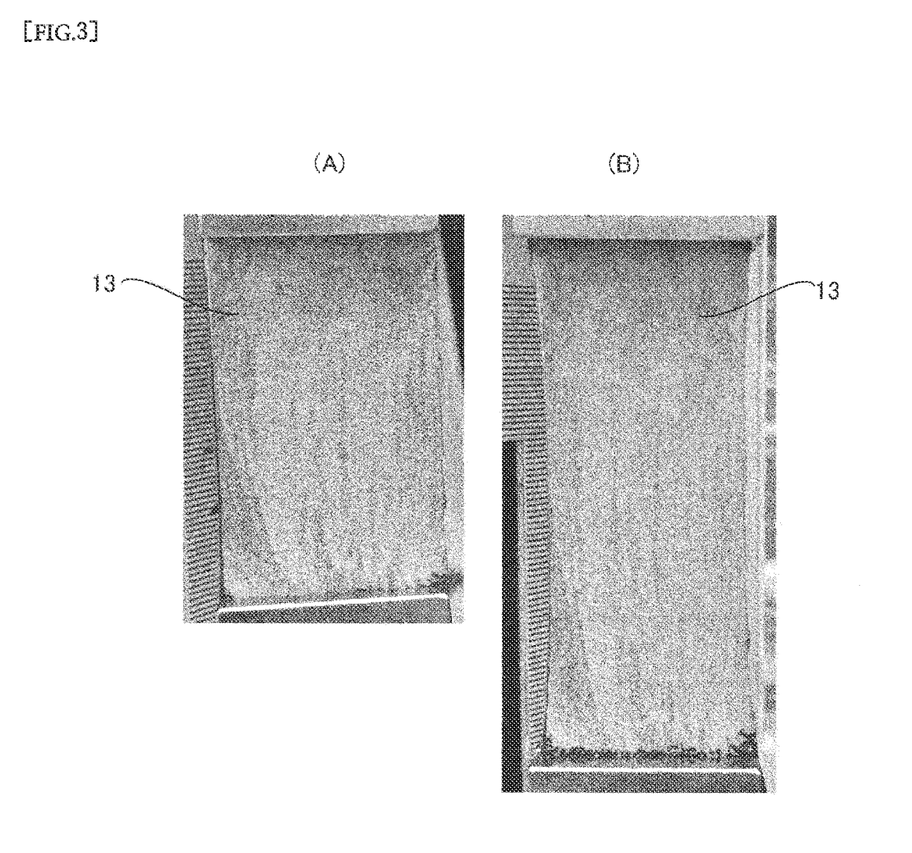
FIG. 3 shows images illustrating the results of the test on film flexibility.
Figure 4:
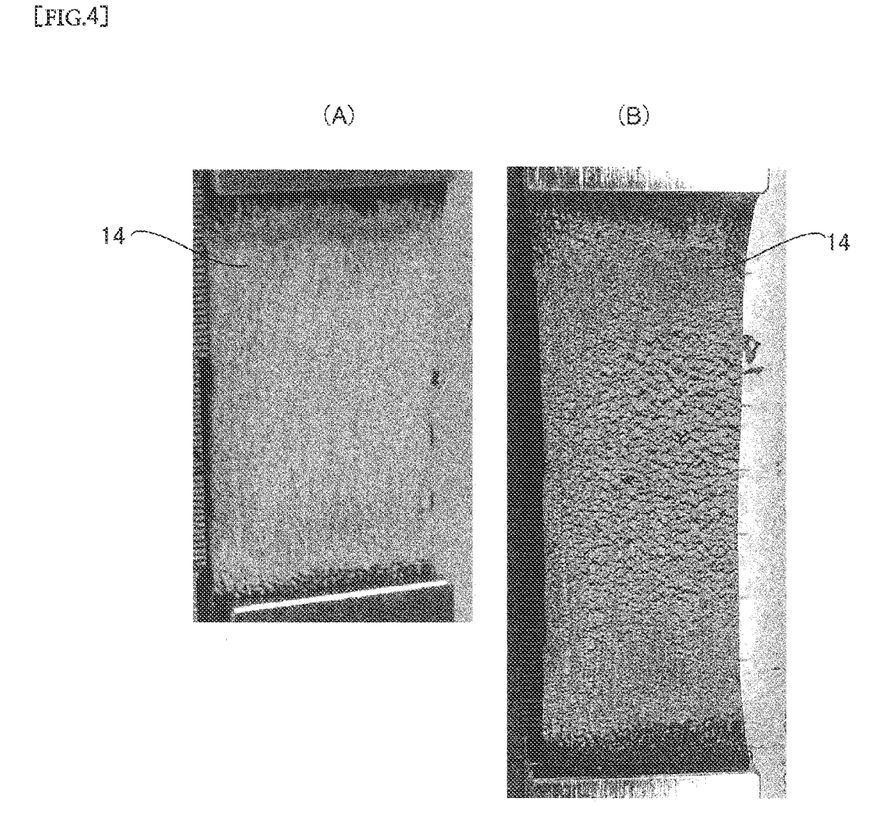
FIG. 4 shows images illustrating the results of the test on film flexibility.
Figure 5:
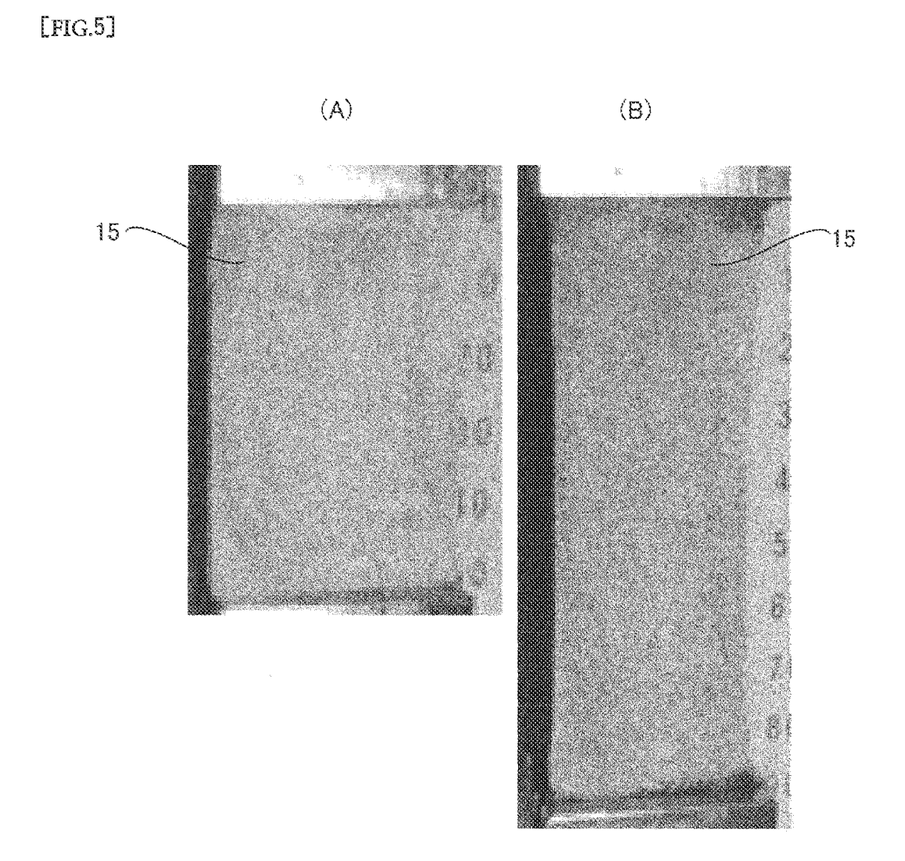
FIG. 5 shows images illustrating the results of the test on film flexibility.
Figure 6:
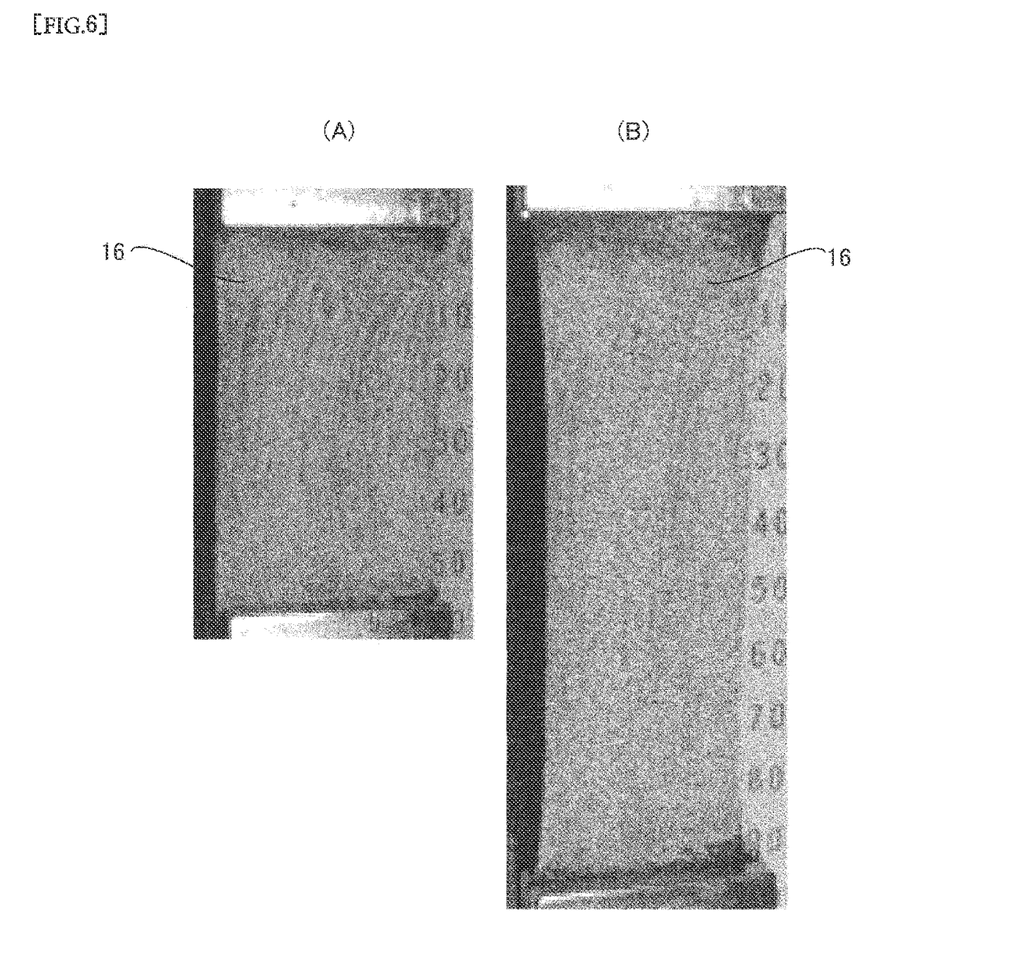
FIG. 6 shows images illustrating the results of the test on film flexibility.

First, the artificial skin made of urethane of 2 mm thick (manufactured by BEAULAX CO., LTD., skin model No. 77, 2T #black) as discussed above was cut into rectangular pieces of 30 mm×70 mm, and 0.05 g of each sample (Examples 1 and 2 and Comparative Examples 3 to 6) was uniformly applied to the surface of 30 mm×50 mm and dried at room temperature for 30 minutes or longer, to thereby prepare test pieces. Using Rheo Meter CR-100 manufactured by SUN SCIENTIFIC CO., LTD., each test piece was fixed with the fixtures for tensile test in 10 mm of the non-applied regions in its upper and lower portions in the longitudinal direction, and moved downwards at a stage speed of 20 mm/min, and the state when the test piece was stretched for 20 mm (140%) was observed. The judgement was made by the standard below. The results of film flexibility are shown in Table 4 and FIGS. 1 to 6. In each of FIGS. 1 to 6, (A) is an image of the test piece before stretching, and (B) is an image of the test piece after stretching. FIG. 1 shows the test piece to which sample 11 of Example 1 was applied. FIG. 2 shows the test piece to which sample 12 of Example 2 was applied. FIG. 3 shows the test piece to which sample 13 of Comparative Example 3 was applied. FIG. 4 shows the test piece to which sample 14 of Comparative Example 4 was applied. FIG. 5 shows the test piece to which sample 15 of Comparative Example 5 was applied. FIG. 6 shows the test piece to which sample 16 of Comparative Example 6 was applied.

| [Judgement] |  |
| --- | --- |
| 5 | No fissures of the makeup film was observed, and the black base of the artificial skin was concealed. |
| 3 | Fissures of less than 1 mm width were observed, and the black base was seen. |
| 1 | Fissures of 1 mm or wider were observed |

(Skin Texture Scoring Based on Image Analysis)

A moderate amount of each sample (Examples 1 and 2 and Comparative Examples 3 to 6) was applied to the faces (right and left cheeks) of two females in their 20s, images were taken with a skin analysis imaging system VISIA EVOLUTION (manufactured by Canfield Scientific, Inc.), and the skin texture (texture) scoring, which is an index of skin smoothness, was calculated using an accompanying analysis software. The images were taken with one sample being applied to four locations on each of the right and left cheeks (8 locations in total). And the images were taken for each sample (Examples 1 and 2 and Comparative Examples 3 to 6). The skin texture scoring calculated for one sample was divided by the skin texture scoring calculated for the sample free of cellulose nanofibers that was applied to the same location of the same subject, and the obtained value was taken as a T value.

($T$ value)=(Skin texture scoring calculated for each sample (Examples 1 and 2 and Comparative Examples 3 to 6))/(Skin texture scoring calculated in Comparative Example 1)

The T values for the eight locations thus calculated were simply averaged to obtain an average (T) value, and judgement was made by the following standard. The results of the skin texture scoring were shown in Table 4.

| [Judgement] | [Average (T) Value] |
| --- | --- |
| 5 | less than 0.9 |
| 3 | 0.9 or more and less than 1.0 |
| 1 | 1.0 or more |

(Discussion)

It is seen from Table 3 that inclusion of cellulose nanofibers results in suppressed sticky texture and impartment of skin resilience. However, as can be seen from Table 4, with too small an average fiber diameter of the cellulose nanofibers, skin tightness results, and the flexibility of the makeup film is poor.

INDUSTRIAL APPLICABILITY

The present invention may be used as cosmetics, such as foundations and base makeup cosmetics.

DESCRIPTION OF REFERENCE NUMERALS

11 Sample of Example 1
12 Sample of Example 2
13 Sample of Comparative Example 3
14 Sample of Comparative Example 4
15 Sample of Comparative Example 5
16 Sample of Comparative Example 6

The invention claimed is:

1. A cosmetic comprising:
   fibers consisting of cellulose nanofibers having an average fiber diameter of 10 to 1000 nm,
   a surfactant,
   a thickening stabilizer, and
   an oil component,
   wherein the cellulose nanofibers have not been subjected to oxidation treatment, and a B-type viscosity of a dispersion of the cellulose nanofibers at 1.5% concentration is 1000 to 5000 cps, and
   wherein the cosmetic comprises 0.01 to 3 mass % of the cellulose nanofibers, and 1 to 50 mass % of the oil component.

2. The cosmetic according to claim 1, wherein a variation coefficient of fiber diameter distribution of the cellulose nanofibers is 1.1 or less.

3. The cosmetic according to claim 2, wherein a peak value of a pseudo particle size distribution curve of the cellulose nanofibers is 1 to 100 μm, and an accumulated volume fraction of nanofibers having a particle size of 100 μm or smaller of the cellulose nanofibers is 90% or more.

4. The cosmetic according to claim 2, wherein the cosmetic is a base makeup cosmetic.

5. The cosmetic according to claim 1, wherein a peak value of a pseudo particle size distribution curve of the cellulose nanofibers is 1 to 100 μm, and an accumulated volume fraction of nanofibers having a particle size of 100 μm or smaller of the cellulose nanofibers is 90% or more.

6. The cosmetic according to claim 5, wherein the cosmetic is a base makeup cosmetic.

7. The cosmetic according to claim 1, wherein the cosmetic is a base makeup cosmetic.

8. The cosmetic according to claim 1, further comprising a UV scattering agent treated with a silicone compound,
   wherein a content of the thickening stabilizer is 0.01 to 5 mass %.

9. The cosmetic according to claim 1, wherein a water retention of the cellulose nanofibers is 300 to 480%.

10. The cosmetic according to claim 1, further comprising a UV scattering agent composed of metal oxide which has been subjected to hydrophobic treatment.

11. The cosmetic according to claim 10, wherein the UV scattering agent is one or a combination of two or more members selected from the group consisting of titanium oxide, zinc oxide, and cerium oxide, all having an average particle size of 100 nm or smaller.

12. The cosmetic according to claim 1,
    wherein the cosmetic has an aqueous phase and an oil phase,
    wherein an oil-soluble film-forming agent is contained in the oil phase, and
    wherein the oil-soluble film-forming agent is partially cross-linked organopolysiloxane.

13. The cosmetic according to claim 12, wherein the cosmetic comprises 0.1 to 5 mass % of the oil-soluble film-forming agent.

14. The cosmetic according to claim 1, wherein a pulp viscosity of the cellulose nanofibers is 3 to 8 cps, and a raw material pulp for the cellulose nanofibers is chemical pulp.

15. The cosmetic according to claim 14, wherein the chemical pulp is softwood bleached kraft pulp.

16. The cosmetic according to claim 1, wherein the surfactant comprises a nonionic surfactant.

17. The cosmetic according to claim 1, further comprising powder, wherein the powder comprises one or a combination of two or more members selected from the group consisting of red iron oxide, yellow iron oxide, and black iron oxide.

18. A cosmetic comprising:
    fibers consisting of cellulose nanofibers,
    a surfactant,
    a thickening stabilizer, and
    an oil component,
    wherein the cellulose nanofibers have not been subjected to oxidation treatment, and a B-type viscosity of a dispersion of the cellulose nanofibers at 1.5% concentration is 1000 to 5000 cps, and
    wherein the cosmetic comprises 0.01 to 3 mass % of the cellulose nanofibers, and 1 to 50 mass % of the oil component, and
    wherein the thickening stabilizer is one or a combination of two or more members selected from the group consisting of (PEG-240/decyltetradeceth-20/HDI) copolymers, (sodium acrylate/acryloyldimethyltaurate) copolymers, (hydroxyethyl acrylate/sodium acryloyldimethyl taurate) copolymers, (ammonium acryloyldimethyltaurate/VP) copolymers, and (ammonium acryloyldimethyltaurate/beheneth-25 methacrylate) crosspolymers.

* * * * *